(12) United States Patent
Kurata

(10) Patent No.: US 6,840,929 B2
(45) Date of Patent: Jan. 11, 2005

(54) DISPOSABLE WORN ABSORBENT ARTICLE INCLUDING STAND-UP CUFFS

(75) Inventor: Syuhei Kurata, Kyoto (JP)

(73) Assignee: Zuiko Corporation, Osaka (JP)

( * ) Notice: Subject to any disclaimer, the term of this patent is extended or adjusted under 35 U.S.C. 154(b) by 357 days.

(21) Appl. No.: 10/120,276

(22) Filed: Apr. 10, 2002

(65) Prior Publication Data

US 2003/0093056 A1 May 15, 2003

(30) Foreign Application Priority Data

Nov. 14, 2001 (JP) ........................................ 2001-348848

(51) Int. Cl.$^7$ .............................................. A61F 13/15
(52) U.S. Cl. .................................................. 604/385.28
(58) Field of Search ....................... 604/385.01, 385.24, 604/385.25, 385.28

(56) References Cited

U.S. PATENT DOCUMENTS

| 4,904,251 | A | | 2/1990 | Igaue et al. | |
| 5,064,489 | A | * | 11/1991 | Ujimoto et al. | 156/164 |
| 5,445,628 | A | * | 8/1995 | Gipson et al. | 604/392 |
| 5,643,377 | A | * | 7/1997 | Juergens | 156/73.1 |
| 5,662,636 | A | * | 9/1997 | Benjamin et al. | 604/385.28 |
| 6,174,302 | B1 | * | 1/2001 | Kumasaka | 604/385.28 |
| 6,629,967 | B1 | | 10/2003 | Simmons et al. | |
| 2004/0153044 | A1 | * | 8/2004 | Kuen et al. | 604/385.28 |

FOREIGN PATENT DOCUMENTS

| EP | 1 101 470 A3 | 11/2000 |
| EP | 1 101 470 A2 | 11/2000 |
| GB | 2 284 538 A | 6/1995 |
| WO | WO 98/37842 | 9/1998 |

* cited by examiner

Primary Examiner—Larry I. Schwartz
Assistant Examiner—Michael G. Bogart
(74) Attorney, Agent, or Firm—Renner, Otto, Boisselle & Sklar, LLP

(57) ABSTRACT

A disposable worn article N comprises an absorbent body M including a core C and a liquid impermeable backsheet B, and a cuff 10 including a contact portion 12 and a stand-up portion 11. In the vicinity of a central portion of the cuff 10, a free end 123 of the contact portion 12 and a connecting portion 13 between the contact portion 12 and the stand-up portion 11 are arranged in the order of the free end 123 and the connecting portion 13 in a direction that transverses a direction in which the cuff 10 extends and that extends from an inside to an outside of the absorbent body M. In the vicinity of an end portion of the cuff 10, the free end 123 and the connecting portion 13 are arranged in the order of the connecting portion 13 and the free end 123 in the direction that transverses the direction in which the cuff 10 extends and that extends from the inside to the outside of the absorbent body M.

16 Claims, 7 Drawing Sheets

DISPOSABLE WORN ABSORBENT ARTICLE INCLUDING STAND-UP CUFFS

FIELD OF THE INVENTION

The present invention relates primarily to a disposable worn article such as a disposable diaper, disposable pants, a sanitary napkin, or an incontinence pad.

BACKGROUND OF THE INVENTION

In recent years, worn articles of this type with a cuff 100, as illustrated in FIG. 7A or FIG. 7B, being provided around the legs or on both sides of the genitals of the wearer, are known in the art (see, for example, Japanese Patent No. 2540495, Japanese Patent Publication for Opposition No. 6-93901,and International Publication WO01/05347). These cuffs 100 prevent a body fluid such as excrement from leaking from the sides.

However, with the cuff 100 of FIG. 7A, only an edge portion 101 in the cuff 100 is in contact with the surface of the wearer, but it is less likely to be brought into a planar contact therewith, whereby the function of preventing a body fluid from leaking from the sides is low.

On the other hand, with the cuff 100 of FIG. 7B, a contact portion 103 that extends outwards from a stand-up portion 102 is brought into a planar contact with the surface of the wearer, thereby relatively enhancing the side leak preventing function.

However, while a body fluid L such as excrement or urine is urged to flow outwards with a great force at the moment of excretion, etc., as indicated by a broken line, the flow L moves from the stand-up portion 102 onto the inner surface of the contact portion 103, whereby the body fluid L may move along the surface of the contact portion 103 and leak from the sides.

Moreover, since the stand-up portion 102 is facing outwards, the body fluid L may possibly move along the stand-up portion 102 to soil the outer wear of the wearer.

SUMMARY OF THE INVENTION

Thus, an object of the present invention is to provide a disposable worn article which has a side leak preventing function. Another object of the present invention is to provide a disposable worn article with which a body fluid is not likely to move to the outside of the worn article.

A cuff of a worn article of the present invention includes: a strip-shaped elongate stand-up portion that is standing up with respect to the inner surface of the worn article when the worn article is worn; a strip-shaped contact portion which contacts the surface of the wearer and which is provided continuously with the stand-up portion so as to protrude from the stand-up portion in an inward direction perpendicular to the longitudinal direction of the cuff when the worn article is worn; and a folded portion which is folded so that the contact portion is positioned inwards with respect to the stand-up portion when the worn article is worn. This worn article is defined while focusing on its normal state.

In another embodiment, a cuff of a disposable worn article of the present invention has an elasticity in the longitudinal direction of the cuff, and includes: a strip-shaped first portion that protrudes in an inward direction generally perpendicular to the longitudinal direction of the cuff in a stretched state where the disposable worn article is stretched in the longitudinal direction; and a strip-shaped second portion that is provided continuously with an inner edge portion of the first portion and that is folded so as to be sandwiched between the first portion and the absorbent body in the stretched state. The second portion is attached to the inner surface of the worn article at each end portion thereof in the longitudinal direction, and the second portion can float from the topsheet in an intermediate portion between the end portions. This worn article is defined while focusing on its stretched state where the cuff is stretched.

In another embodiment, an elastic cuff of the present invention includes: a strip-shaped first portion whose outer edge portion along the longitudinal direction is fixed to the inner surface side of the worn article; and a strip-shaped second portion that is continuous with an inner edge portion of the first portion, wherein: each end portion of the second portion in the longitudinal direction is sandwiched between each end portion of the first portion in the longitudinal direction and the inner surface of the worn article, and is attached to the inner surface of the worn article; and the cuff is twisted so that an intermediate portion of the first portion in the longitudinal direction stands up with respect to the inner surface of the worn article by the elasticity that urges the cuff to shrink in the longitudinal direction, while the front and backsides of the second portion are reversed between the intermediate portion and the end portion in the longitudinal direction by the elasticity of the cuff.

A disposable worn article of the present invention includes an absorbent body including a core and a liquid impermeable backsheet, and a cuff including a contact portion and a stand-up portion. The contact portion is connected to the stand-up portion. In the vicinity of a central portion of the cuff, a free end of the contact portion and a connecting portion between the contact portion and the stand-up portion are arranged in the order of the free end and the connecting portion in a direction that transverses a direction in which the cuff extends and that extends from the inside to the outside of the absorbent body. In the vicinity of an end portion of the cuff, the free end and the connecting portion are arranged in the order of the connecting portion and the free end in the direction that transverses the direction in which the cuff extends and that extends from the inside to the outside of the absorbent body. Such a cuff may be used in, for example, the front part of a male disposable diaper. Alternatively, it may be used in combination with a general leak preventing wall (cuff). Note that a disposable worn article of the present invention may include a plurality of cuffs.

An air permeable, water repellant material is preferably used for the cuffs (cuff), so that the humidity inside is reduced while the body fluid in the cuff is prevented from leaking to the outside. However, in a case where the absorbent body includes a liquid impermeable backsheet and a liquid permeable topsheet, the cuff may include at least the backsheet and/or the topsheet. Moreover, in a case where the absorbent body is covered with a cover sheet, the cuff may include at least the cover sheet.

Moreover, the width of the stand-up portion or the first portion may be 5 mm to 60 mm. Moreover, the width of the contact portion or the second portion may be 5 mm to 40 mm. These widths are each set in terms of a numerical value measured in a direction generally perpendicular to the direction in which the cuff extends and with the disposable worn article being stretched.

The stand-up portion and the contact portion may be provided with gathers along the longitudinal direction. The gathers of the stand-up portion are useful in maintaining the standing orientation of the stand-up portion. The gathers of the contact portion improve the feel/touch to the wearer.

BRIEF DESCRIPTION OF THE DRAWINGS

FIG. 4A to FIG. 4D each schematically illustrate a cross-sectional view of the diaper, wherein FIG. 4A is a cross-sectional view of an end portion in a stretched state, FIG. 4B is a cross-sectional view of an intermediate portion in a stretched state, FIG. 4C is a cross-sectional view taken along line VIc—VIc in a normal state, and FIG. 4D is a cross-sectional view of an intermediate portion in a normal state.

DESCRIPTION OF THE PREFERRED EMBODIMENTS

An embodiment of the present invention will now be described with reference to the drawings.

Figure 1:
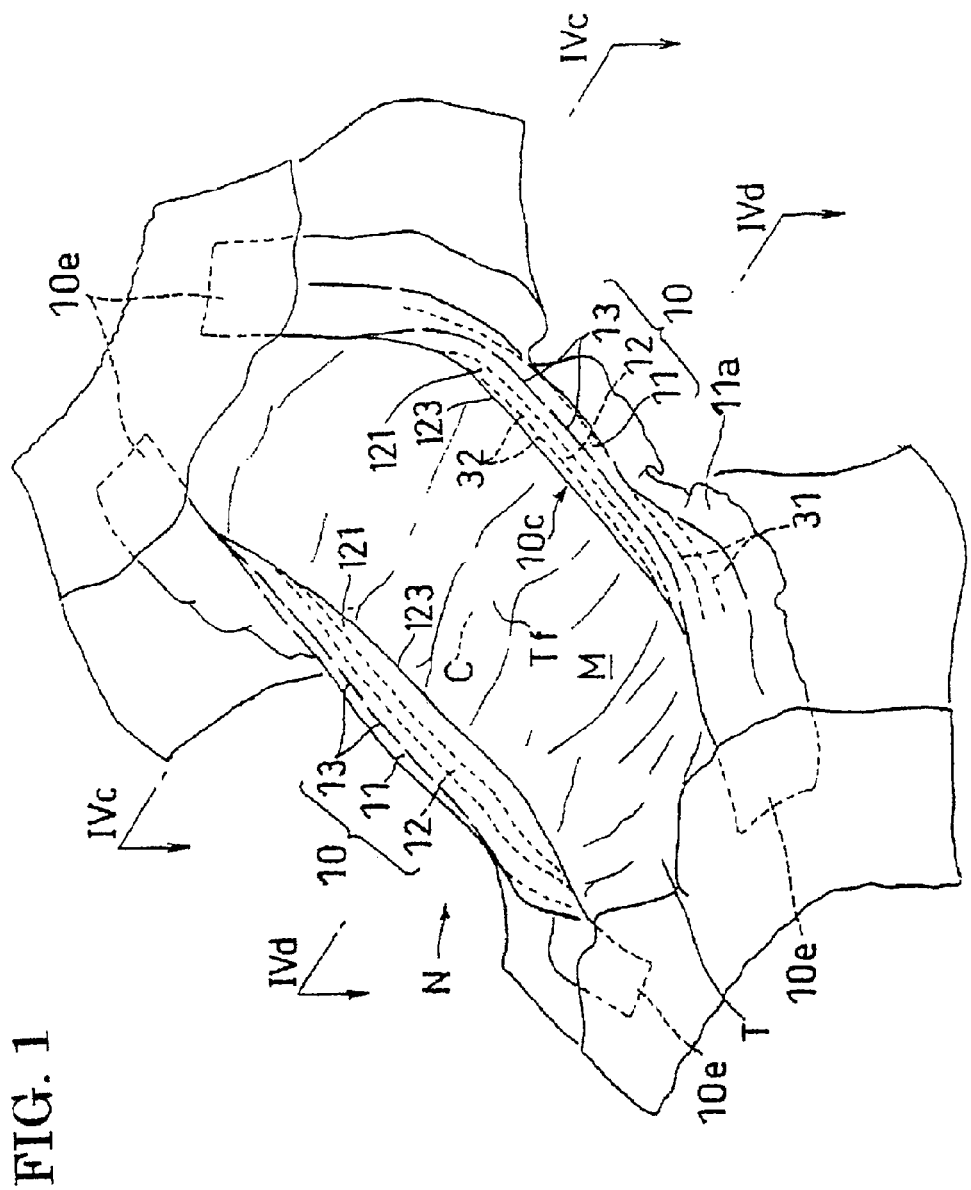
FIG. 1 is a schematic perspective view illustrating a diaper according to an embodiment of the disposable worn article of the present invention, in which gathers are not shown.
Figure 2:
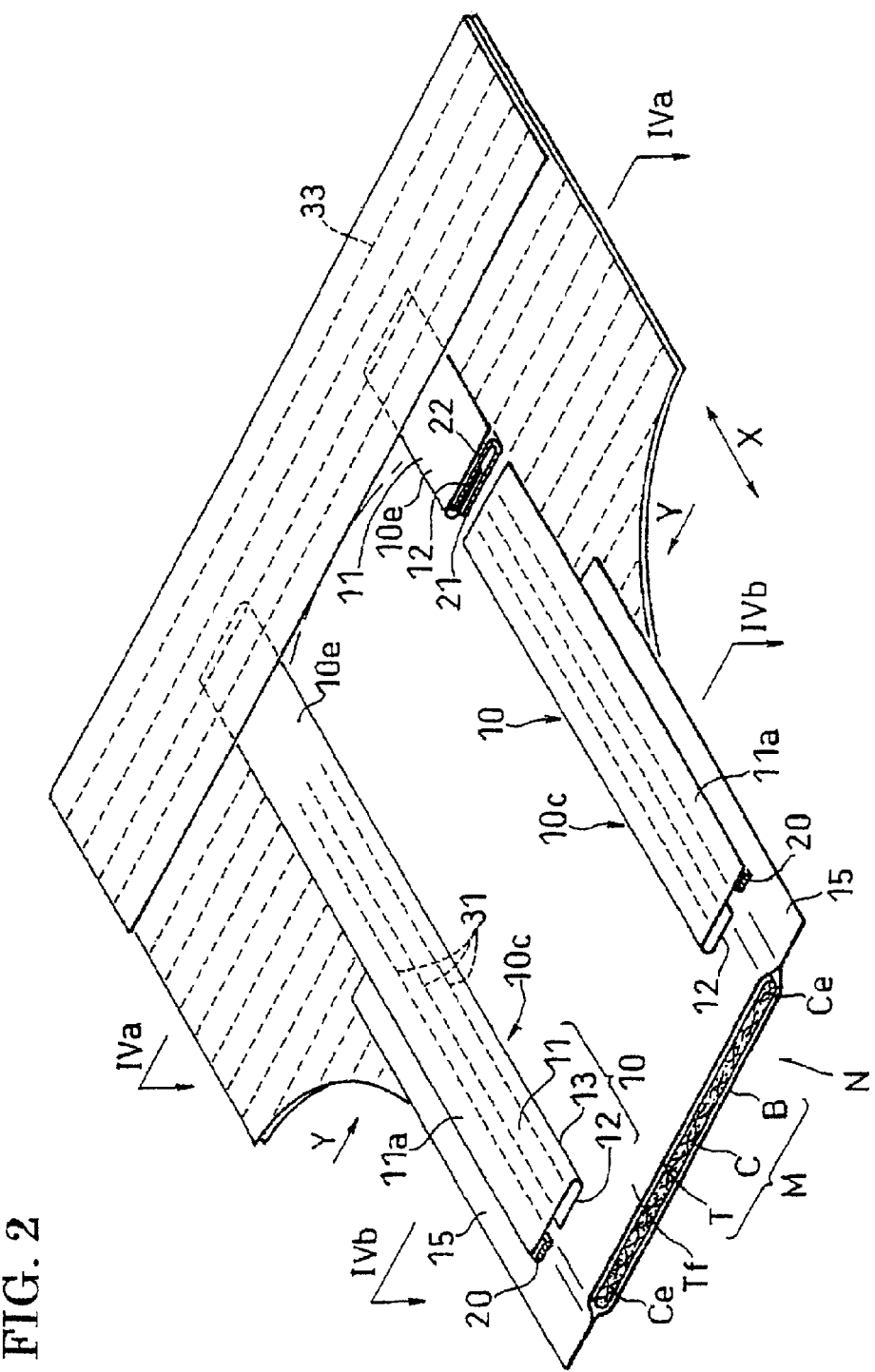
FIG. 2 is a partially cut away perspective view illustrating the diaper being stretched.

FIG. 1 is a perspective view illustrating a disposable worn article such as a diaper, and FIG. 2 is a schematic perspective view illustrating the diaper being partially cut away while being stretched in the length and width directions.

A worn article N includes an absorbent body (body portion) M and a cuff 10. The absorbent body M includes a liquid permeable topsheet T, a liquid impermeable backsheet B (e.g., polyethylene), and a core (e.g., absorbent) C located between the topsheet T and the backsheet B. Note that the absorbent body M is not limited to the configuration described above, as long as it is capable of absorbing a body fluid. For example, the backsheet B may cover an air laid material. Moreover, the backsheet B may be an air permeable, water repellant sheet.

As illustrated in FIG. 2, edge portions 15 of the topsheet T and the backsheet B are attached to each other via heat sealing (or ultrasonic seal) or a hot melt resin, and the topsheet T and the backsheet B surround the core C. The core C may be fluff pulp obtained by spreading pulp with a spreader (or mill) into a fibrous form, a material obtained by mixing the fluff pulp with a superabsorbent material (e.g., superabsorbent polymers) and letting it deposit into a cotton-like form, or the like, and the core C has a liquid absorbing property. Note that while FIG. 2 illustrates one end of the cuff 10, the other end of the cuff 10 may have a configuration as that illustrated in FIG. 2.

Figure 3:
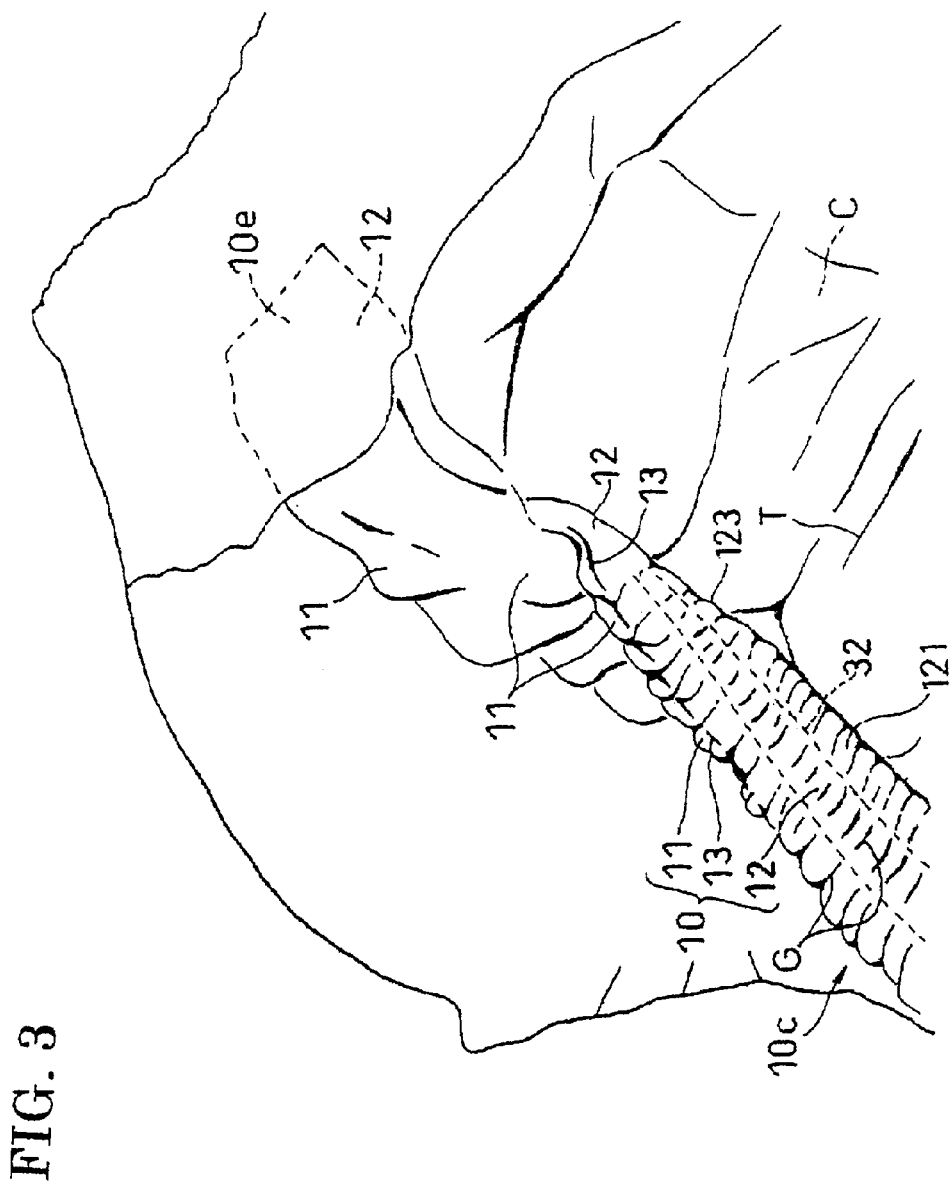
FIG. 3 is a schematic perspective view illustrating an end portion, and the vicinity thereof, of a cuff of the diaper.

The absorbent body M is provided generally in an area covering the crotch of the wearer. A pair of cuffs 10 and 10 are provided along opposite side edge portions Ce, or the vicinity thereof, of the core C. The cuff 10 has an elasticity in the longitudinal direction X and extends in the longitudinal direction X. As illustrated in FIG. 3, the cuff 10 has gathers G. In order to give an elasticity to the cuff 10, one or more pieces of an elastic member such as a string rubber or a flat rubber may be included in the cuff 10, or the cuff 10 itself may be made of an elastic member.

Note that the string rubber, or the like, the string rubber, or the like, need not necessarily be provided in each end portion 10e of the cuff 10 in the longitudinal direction X. The string rubber at the end portion 10e does not have a significant influence upon twisting the cuff 10, because a part (or all) of the cuff 10 at the end portion 10e is connected with the absorbent body M.

Moreover, in a case where the absorbent body M is covered with a sheet that is longer than the absorbent body M in the inward direction that transverses the longitudinal direction X, the cuff 10 may be provided in the sheet. Thus, the cuff 10 may be used at any position in a disposable worn article in which the absorbent body M, etc., is modified, as long as it is used for the purpose of preventing a body fluid from leaking from the sides.

In a state with no external force acting on the garment, the worn article N may be bent as illustrated in FIG. 1. The cuff 10 includes a first portion 11, a second portion 12 and a folded portion 13 each having a strip shape elongated in the longitudinal direction X. The first portion is attached to, or continuous with, the absorbent body M along each edge portion 15 (FIG. 2) of the absorbent body M, and is connected to (or continuous with) the second portion 12 via the folded portion (connecting portion) 13. At the end portion 10e of the cuff 10 in the longitudinal direction X, the second portion 12 is arranged between the absorbent body M and the first portion 11.

In a normal state (a state with no external force acting on the worn article), in a central portion 10c of the cuff 10 in the longitudinal direction X (e.g., FIG. 4D), the first portion 11 stands up, and the second portion 12 protrudes in the direction that transverses the longitudinal direction X. In a case where the worn article includes a pair of cuffs 10 and 10, each of the second portions 12 protrudes inwards towards one another. Moreover, the second portion 12 has a first surface 121 and a second surface 122, and the first surface 121 of the second portion 12 faces the absorbent body M at the end portion 10e of the cuff 10 (e.g., FIG. 4A), whereas the second surface 122 of the second portion 12 faces the absorbent body M in the central portion 10c in a normal state. Specifically, between the end portion 10e of the cuff 10 and the central portion 10c of the cuff 10, the surface that faces the absorbent body M is switched from one surface of the second portion 12 to the other surface thereof. In other words, the second portion 12 is twisted between the end portion 10e and the central portion 10c. Note that depending on the shrinking force of the cuff 10, the second surface 122 of the second portion 12 of FIG. 4C may not be facing the absorbent body M even in the vicinity of the central portion, i.e., around the central portion 10c, e.g., along the cross section IVc—IVc shown in FIG. 1. In other words, the angle between the first portion 11 and the second portion 12 may be an acute angle or an obtuse angle in the vicinity of the central portion 10c. This is because even if the second portion 12, which is the contact portion, is slightly inclined toward the center of the absorbent body M, the second portion 12 contacts the wearer and the second surface 122 of the second portion 12 faces the absorbent M, whereby there is no problem.

As shown in the cut-away portion of FIG. 2, the second portion 12 may be attached to the absorbent body M, e.g., the topsheet T at each end portion 10e of the cuff 10 in the longitudinal direction X. In an intermediate portion of the cuff 10 in the longitudinal direction X (e.g., the portion of the cuff 10 other than the end portion 10e in the longitudinal direction X), the second portion 12 is not attached to the absorbent body M, e.g., the topsheet T, and can float from the absorbent body M. The first portion 11 may be attached to the second portion 12 via an adhesive 22 at the end portion 10e. Thus the first portion may be attached to the absorbent body M, e.g., the topsheet T, via the second portion 12. Moreover, at the end portion 10e, a portion of the second portion 12 may be wound around its free end 123 as an axis. Note that in a case where a hot melt is used as an adhesive, the hot melt may be applied by using any of beads, a coater, a spiral, a curtain, a spray, a transfer roll, etc. Types of hot melt that can be used include a synthetic rubber-based hot melt, an olefin-based hot melt, etc. Moreover, an adhesive may be applied on the elastic member.

Next, an example of an arrangement of the elastic member, e.g., a string rubber, will be described with reference to FIG. 4A and FIG. 4B.

At least one first string rubber 31 is buried (or inserted) in the first portion 11 along the longitudinal direction X. Moreover, at least one second string rubber 32 is buried (or inserted) in the second portion 12 along the longitudinal direction X.

A shrinking force is applied by the string rubber, or the like, to the first portion 11 and the second portion 12 of the cuff 10, urging these portions to shrink in the longitudinal direction X of FIG. 2. Therefore, in a normal state of a product of the worn article N, or when the worn article N is worn, the first portion 11 stands up, and the second portion 12 rises to be separated from the absorbent body M, e.g., the topsheet T, as will be described below.

Specifically, in the worn article N, being in a stretched state of FIG. 2, the cuff 10 is bent by the shrinking force of the cuff 10 so as to cover a portion of the absorbent body M, whereby the worn article N is bent with the inner surface of the absorbent body M forming a concave shape, in a normal state of FIG. 1. On the other hand, the cuff 10 is arranged along a path of a short distance as the distance from the end portion 10e to the end portion 10e along the cuff 10 is shortened due to the shrinking force.

Figure 4A:
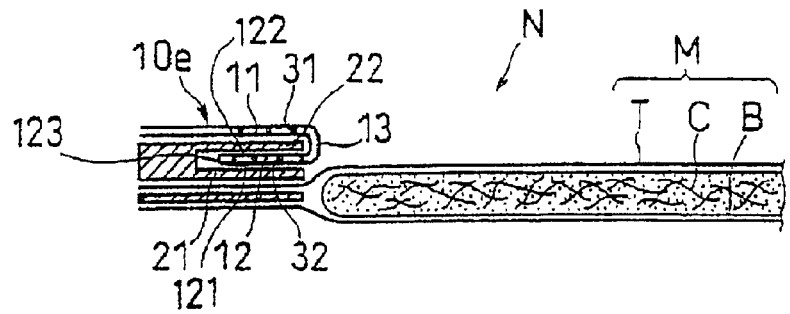
Figure 4B:
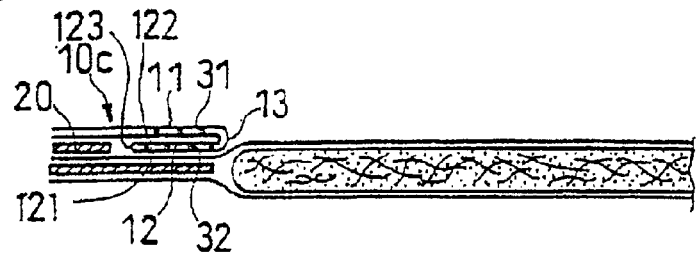
Figure 4C:
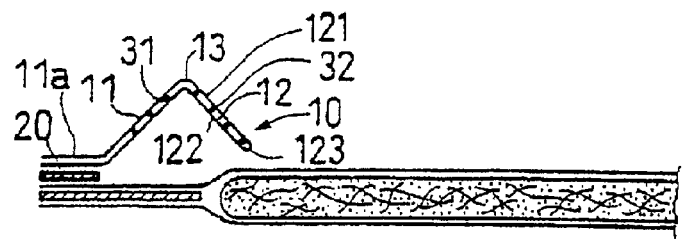
Figure 4D:
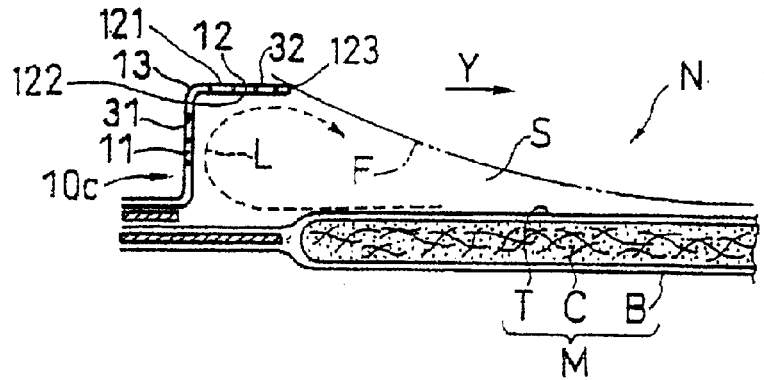

As illustrated in FIG. 4D, the first portion 11 stands up with respect to the absorbent body M, e.g., the topsheet T, in the central portion 10c in the longitudinal direction X. On the other hand, the sides of the second portion 12 are reversed between the end portion 10e (e.g., FIG. 4A) and the vicinity of the central portion 10c (e.g., FIG. 4D), so that the second portion 12 protrudes in the inward direction Y with respect to the first portion 11, in the vicinity of the central portion 10c and the vicinity thereof in the longitudinal direction X. Herein, "inward direction Y" is a direction that transverses a direction in which the cuff extends and that extends from an outside to an inside of the absorbent body. Specifically, in the vicinity of the central portion 10c, the second portion 12 floats from the absorbent body M, and the first surface 121 of the second portion 12 is not facing the absorbent body, due to the shrinking force of the cuff 10. In the vicinity of the central portion, a free end (side edge portion) 123 of the contact portion 12 is located closer to the center of the body M with respect to the folded portion 13, whereas the folded portion 13 is located closer to the center of the body M with respect to the free end 123 of the contact portion 12 at the end portion 10e.

Thus, when the worn article N is worn, the first portion 11 becomes a stand-up portion that stands up with respect to the surface of the absorbent body M, e.g., the topsheet T, while the second portion 12 becomes a contact portion that contacts a surface F of the wearer. As illustrated in FIG. 4D, the contact portion 12, together with the absorbent body M and the stand-up portion 11, may form a space S for holding the body fluid between the portions and the surface F of the wearer.

In the present embodiment, as illustrated in FIG. 4D, when the body fluid L flows outwards with a great force, it is possible that the body fluid L is returned inwards by moving around along the inner surface of the stand-up portion 11 and the inner surface of the contact portion 12. Therefore, a function for preventing a side leak may be provided.

Note that the stand-up portion 11 may be standing up not only by the shrinking force of the first string rubber 31 but also by the shrinking force of the second string rubber 32.

The shrinking force of the contact portion 12 is preferably set to be greater than the shrinking force of the stand-up portion 11. This is because it is then possible to make the contact portion 12 generally parallel to the absorbent body M. Specifically, it is preferably set so that the stress of the second string rubber 32 of FIG. 4B is greater than the stress of the first string rubber 31 in a stretched state as illustrated in FIG. 2. For example, in a case where the first and second string rubbers are the same material or the same structure, the stretch ratio (the amount of stretch per unit length) of the second string rubber 32 can be set to be greater than the stretch ratio of the first string rubber 31. Moreover, in a case where the string rubbers 31 and 32 have generally the same stretch ratio, the second string rubber 32 having a shrinking force greater than the shrinking force of the first string rubber 31 can be used. Thus, the contact portion 12 can be made generally parallel to the absorbent body M by combining different types and stretch ratios of string rubbers.

Moreover, the second string rubber 32 of the contact portion 12 can be arranged at a generally uniform pitch in the Y direction. With a constant interval, it is possible to obtain uniform gathers.

Note that while the description above has been made with respect to the case of a string rubber, the elastic member may be a flat rubber, an elastic film, etc., as described above, or the contact portion and/or the stand-up portion themselves may be elastic, and the description above similarly applies to those cases.

Moreover, in a case where the shrinking force of the contact portion 12 is the same as, or slightly smaller than, the shrinking force of the stand-up portion 11, even if the contact portion 12 is slightly inclined toward the center of the absorbent body M, the contact portion 12 contacts the wearer when the worn article N is worn. Moreover, in a case where the shrinking force of the contact portion 12 and the shrinking force of the stand-up portion 11 are generally the same, a device for supplying a string rubber to a portion to be the contact portion or the stand-up portion while applying a tension on the string rubber can be shared, for example, thereby reducing the production cost of the disposable worn article.

Note that a cuff as described above may be provided so as to extend in the inward direction Y, for example, in the vicinity of an end portion of the core C in the longitudinal direction X, e.g., along at least one of the front part and the back part. With such a cuff or cuffs, it is possible to prevent the body fluid from leaking from the waist portion of the worn article N.

In a case where the topsheet T does not exist at the end portion 10e of the cuff 10 of FIG. 2, the end portion 10e of the cuff 10 may be attached to the core C or the backsheet B. Thus, the end portion 10e of the cuff 10 may be attached (fixed) to the inner surface of the worn article N with the second portion 12 being folded between the first portion 11 and the inner surface of the worn article N.

For the attachment of the attachment portions 20, 21 and 22 of FIG. 4A and FIG. 4B, a hot melt type adhesive may be used, for example. However, it may alternatively be attachment with a heat seal or an ultrasonic seal. Furthermore, it may alternatively be sewing with a string, or the like.

The attachment of the end portion 10e of the cuff 10 may be provided as illustrated in FIG. 5A to FIG. 5D.

Figure 5A:
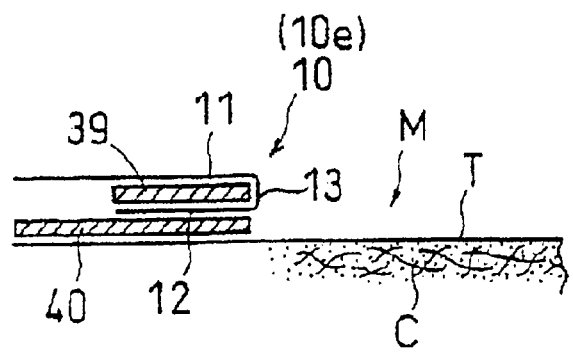
FIG. 5A to FIG. 5D are each a cross-sectional view illustrating an alternative attachment of the cuff.

According to an example of a method for producing a cuff illustrated in FIG. 5A, the adhesive 39 is applied on at least one of the first portion 11 and the second portion 12, and the first portion 11 and the second portion 12 are folded along the folded portion 13. Then, at least the second portion 12 is connected to (attached to while being laid over) the absorbent body M, e.g., the topsheet T, by an adhesive 40. Note that the first portion 11 may be connected to the absorbent body M via the second portion 12 by an adhesive, as illustrated in FIG. 5A. Moreover, a heat seal or an ultrasonic seal may be used instead of the adhesive 40.

Figure 5B:
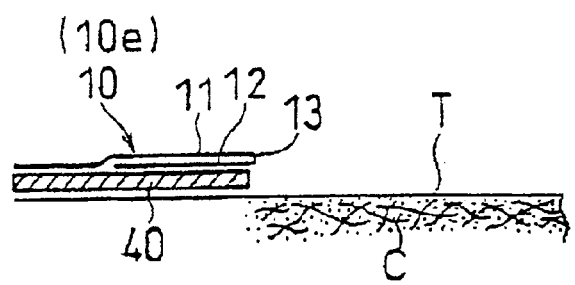

According to an example of a method for producing a cuff illustrated in FIG. 5B, the first portion 11 and the second portion 12 are folded along the folded portion 13. Then, at least the second portion 12 is connected to the absorbent body M, e.g., the topsheet T, by the adhesive 40. Note that the first portion 11 maybe connected to the absorbent body M except for at least the second portion 12 by an adhesive, as illustrated in FIG. 5B. Moreover, a heat seal or an ultrasonic seal may be used instead of an adhesive.

Figure 5C:
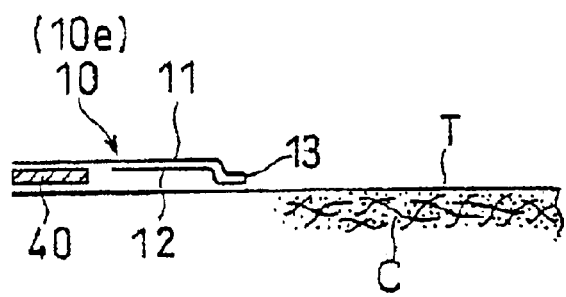

According to an example of a method for producing a cuff illustrated in FIG. 5C, the first portion 11 and the second portion 12 are folded along the folded portion 13, and a heat seal is applied to the vicinity of the folded portion 13. Thus, the first portion 11 is connected to the absorbent body M, e.g., the topsheet T, via at least a portion of the second portion 12. Note that the first portion 11 may be connected to the absorbent body M via the vicinity of the folded portion 13 by an adhesive, as illustrated in FIG. 5C. Moreover, a heat seal or an ultrasonic seal may be used instead of an adhesive.

Figure 5D:
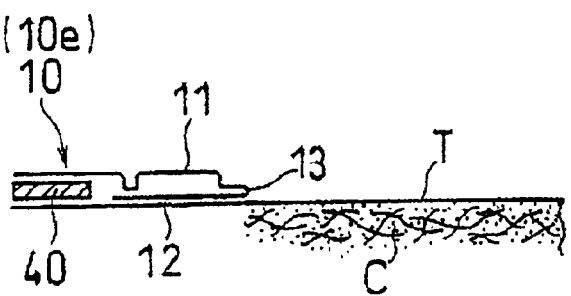

According to an example of a method for producing a cuff illustrated in FIG. 5D, the first portion 11 and the second portion 12 are folded along the folded portion 13, and the vicinity of the folded portion 13 and the vicinity of the free end of the second portion 12 are heat sealed together. Thus, the first portion 11 and the second portion 12 are connected to the absorbent body M, e.g., the topsheet T. Note that the first portion 11 may be connected to the absorbent body M via the vicinity of the folded portion 13, etc., by an adhesive, as illustrated in FIG. 5D. Moreover, a heat seal or an ultrasonic seal may be used instead of an adhesive.

In a case where the backsheet is covered with a cover sheet, cuffs as described above may be produced by using the cover sheet. In this way, the absorbent body M and the cuffs as described above can be formed integrally.

Figure 6A:
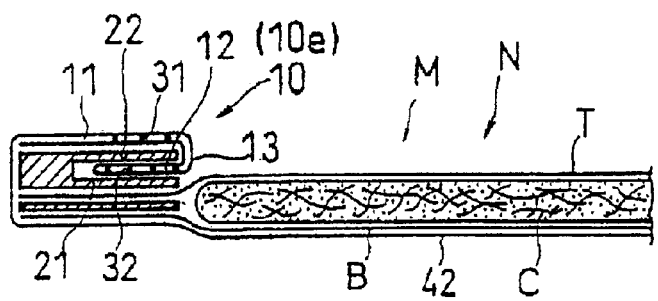
FIG. 6A to FIG. 6C are each a cross-sectional view illustrating an alternative structure of a disposable worn article.
Figure 6B:
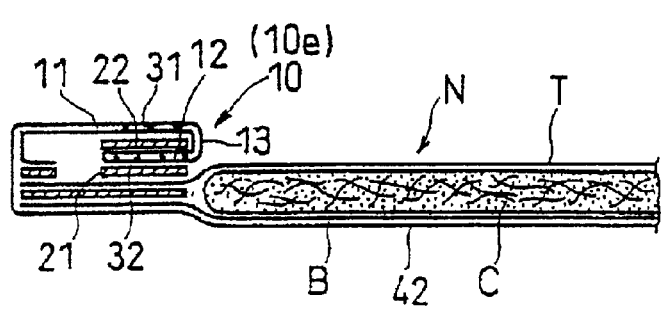
Figure 6C:
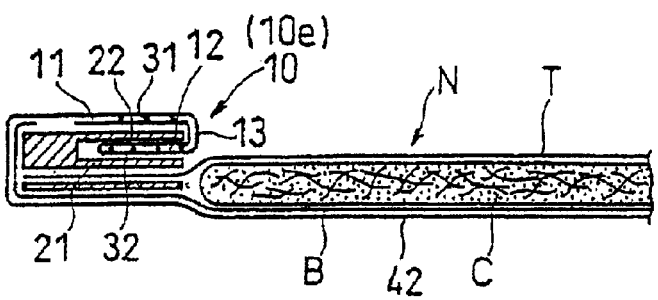
Figure 7A:
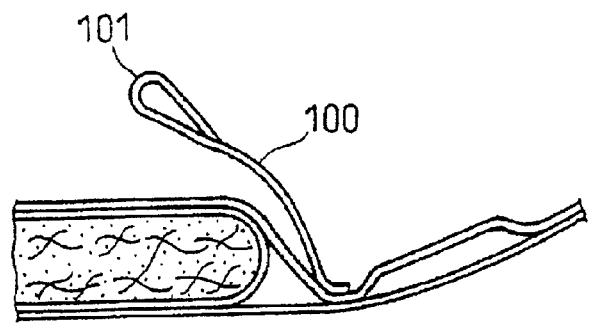
FIG. 7A and FIG. 7B are each a cross-sectional view illustrating a structure of a conventional cuff.
Figure 7B:
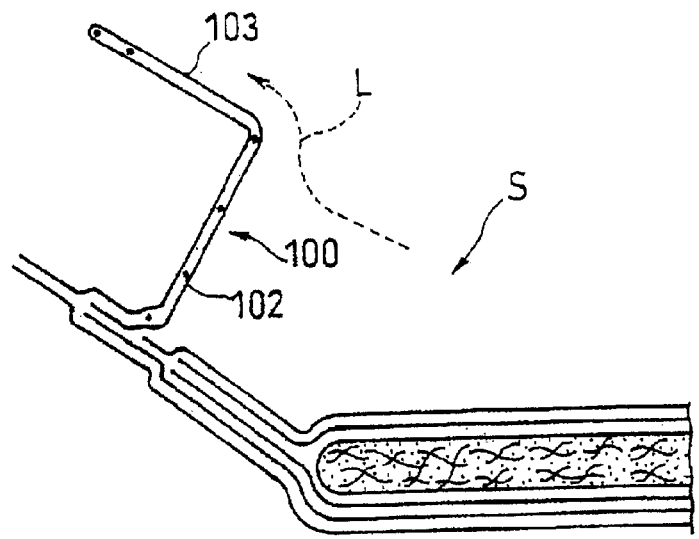

FIG. 6A to FIG. 6C are diagrams illustrating an example where a cuff is formed by using a cover sheet, etc. In FIG. 6A and FIG. 6B, the absorbent body M is placed in the vicinity of the generally central portion of a cover sheet 42 that is longer than the absorbent body M in the inward direction Y, and the cuff 10 as described above is formed by using an end portion of the cover sheet that is present outside the absorbent body M.

For example, in the cuffs 10 illustrated in FIG. 6A and FIG. 6B, the elastic member is sandwiched by the folded-back cover sheet. Particularly, in the cuff 10 illustrated in FIG. 6B, a tip portion of the folded-back cover sheet is attached to the absorbent body M. With such a configuration, the rigidity of the cuff 10 is increased.

The cuff of FIG. 6C is made by using the cover sheet 42 as described above, and the backsheet B is arranged over a portion or a whole of the first portion 11. Thus, it is possible to reduce the leak of the body fluid from a portion or a whole of the first portion 11. Note that depending on the specifications, the backsheet may be arranged to reach the second portion 12. Specifically, an elastic member is arranged between the cover sheet and the backsheet. However, the backsheet does not need to extend from the second surface of the second portion 12 to the first surface 121 thereof. This is because the backsheet may then directly contact the wearer when the worn article N is worn.

As described above, in a disposable worn article of the present invention, the stand-up portion stands up and the contact portion protrudes toward a position around the center of the absorbent body at least in the vicinity of the central portion of the cuff, whereby there is a reduced possibility that the body fluid moves along the contact portion to soil the underwear of the wearer, as compared to a disposable worn article in which the contact portion extends to the outside of the absorbent body.

Moreover, even if the body fluid flows with a great force toward the absorbent body, for example, the body fluid can easily be returned by the stand-up portion and the contact portion toward the absorbent body. Therefore, with a disposable worn article of the present invention, there is a reduced possibility that the body fluid leaks to the outside, as compared to a disposable worn article in which the contact portion extends to the outside of the absorbent body.

Moreover, in the case of another disposable worn article of the present invention including, together with the absorbent body, cuffs projecting toward the central portion of the absorbent body, the projecting second portions can be brought into a planar contact with the wearer, whereby excrement, etc., can be confined in the space formed by the cuffs and the absorbent body.

What is claimed is:

1. A disposable worn article, comprising an absorbent body including a core and a liquid impermeable backsheet, and a cuff including a contact portion and a stand-up portion, wherein:

the contact portion is connected to the stand-up portion;

in the vicinity of a central portion of the cuff, a free end of the contact portion and a connecting portion between the contact portion and the stand-up portion are arranged in the order of the free end and the connecting portion in a direction that transverses a direction in which the cuff extends and that extends from an inside to an outside of the absorbent body; and in the vicinity of an end portion of the cuff, the free end and the connecting portion are arranged in the order of the connecting portion and the free end in the direction that transverses the direction in which the cuff extends and that extends from the inside to the outside of the absorbent body.

2. A disposable worn article according to claim 1, wherein:

the disposable worn article comprises a cover sheet that is wider than a width of the absorbent body; and the contact portion and the stand-up portion are formed at least by the cover sheet.

3. A disposable worn article according to claim 1, wherein a portion of the backsheet is included in the stand-up portion.

4. A disposable worn article according to claim 2, wherein a portion of the backsheet is included in the stand-up portion.

5. A disposable worn article according to claim 1, wherein the stand-up portion and the contact portion each include an elastic member, and a stress of the elastic member of the contact portion is equal to or greater than a stress of the elastic member of the stand-up portion in a state where the cuff is stretched.

6. A disposable worn article according to claim 2, wherein the stand-up portion and the contact portion each include an elastic member, and a stress of the elastic member of the contact portion is equal to or greater than a stress of the elastic member of the stand-up portion in a state where the cuff is stretched.

7. A disposable worn article according to claim 1, wherein the cuff is attached to the absorbent body by an adhesive.

8. A disposable worn article according to claim 2, wherein the cuff is attached to the absorbent body by an adhesive.

9. A disposable worn article according to claim 1, wherein:
   the disposable worn article further comprises another cuff; and
   at least one pair of cuffs are arranged in the vicinity of opposite end portions of the core.

10. A disposable worn article according to claim 2, wherein:
    the disposable worn article further comprises another cuff; and
    at least one pair of cuffs are arranged in the vicinity of opposite end portions of the core.

11. A disposable worn article according to claim 4, wherein:
    the disposable worn article further comprises another cuff; and
    at least one pair of cuffs are arranged in the vicinity of opposite end portions of the core.

12. A disposable worn article according to claim 5, wherein:
    the disposable worn article further comprises another cuff; and
    at least one pair of cuffs are arranged in the vicinity of opposite end portions of the core.

13. A disposable worn article, comprising an absorbent body and cuffs, each of the cuffs including a first portion and a second portion, wherein:
    the cuff is arranged in the vicinity of each end portion of the absorbent body;
    the second portion has a first surface and a second surface;
    at an end portion of the cuff, the second portion is arranged between the first portion and the absorbent body, and the first surface of the second portion faces the absorbent body; and
    in the vicinity of a central portion of the cuff, the second portion floats from the absorbent body by a shrinking force of the cuff, and the first surface of the second portion faces a surface different from the absorbent body.

14. A disposable worn article according to claim 13, wherein the cuffs are arranged on the absorbent body so that a wearer, the cuffs and the absorbent body together form a space when the disposable worn article is worn.

15. A disposable worn article according to claim 13, wherein the first portion and the second portion each include an elastic member, and a stress of the elastic member of the second portion is equal to or greater than a stress of the elastic member of the first portion in a state where the cuff is stretched.

16. A disposable worn article according to claim 14, wherein the first portion and the second portion each include an elastic member, and a stress of the elastic member of the second portion is equal to or greater than a stress of the elastic member of the first portion in a state where the cuff is stretched.

* * * * *